(12) United States Patent
Landowski

(10) Patent No.: US 8,603,011 B2
(45) Date of Patent: Dec. 10, 2013

(54) SURGICAL GUIDE WIRE PLACEMENT AND REMOVAL TOOL

(76) Inventor: Steven S. Landowski, Kenosha, WI (US)

( * ) Notice: Subject to any disclaimer, the term of this patent is extended or adjusted under 35 U.S.C. 154(b) by 488 days.

(21) Appl. No.: 12/401,943

(22) Filed: Mar. 11, 2009
(Under 37 CFR 1.47)

(65) Prior Publication Data
US 2010/0022917 A1    Jan. 28, 2010

Related U.S. Application Data

(60) Provisional application No. 60/036,195, filed on Mar. 13, 2008.

(51) Int. Cl.
*A61B 19/00* (2006.01)
*A61M 25/00* (2006.01)

(52) U.S. Cl.
USPC .......................... 600/585; 604/528

(58) Field of Classification Search
USPC ............. 600/585; 269/1–6; 81/300–427.5; 604/528
See application file for complete search history.

(56) References Cited

U.S. PATENT DOCUMENTS

| | | | | | |
|---|---|---|---|---|---|
| 3,302,929 | A | * | 2/1967 | Danielson et al. | 254/134.3 R |
| 5,325,868 | A | * | 7/1994 | Kimmelstiel | 600/585 |
| 5,690,645 | A | * | 11/1997 | Van Erp | 606/108 |
| 7,011,635 | B1 | * | 3/2006 | Delay | 600/585 |
| 7,144,378 | B2 | * | 12/2006 | Arnott | 600/585 |

* cited by examiner

*Primary Examiner* — Max Hindenburg
*Assistant Examiner* — Jonathan M Foreman
(74) *Attorney, Agent, or Firm* — Boyle Fredrickson S.C.

(57) ABSTRACT

A guide wire placement and removal tool is provided that includes a handle mounted to a shaft connected to a wire engagement mechanism disposed opposite the handle. The mechanism includes a housing aligned with the shaft to enable the wire to pass therethrough, and a moveable engagement member biased into a locking position within the housing to engage a wire positioned therein. The mechanism also includes a release member that can be selectively engaged with the engagement member to disengage the engagement member from the wire to allow the wire to move with regard to the tool. Once the release member is released, the engagement member is biased back into a locking engagement with the wire to securely hold the wire within the tool.

9 Claims, 3 Drawing Sheets

SURGICAL GUIDE WIRE PLACEMENT AND REMOVAL TOOL

CROSS-REFERENCE TO RELATED APPLICATION

This application claims priority from U.S. Provisional Patent Application Ser. No. 60/036,195 filed on Mar. 13, 2008, the entirety of which is expressly incorporated by reference herein.

FIELD OF THE INVENTION

The present invention relates to surgical tool, and more specifically to a tool capable of placing and removing guide wires utilized in surgical procedures.

BACKGROUND OF THE INVENTION

In many surgical procedures, screws or other types of fasteners are utilized to hold pieces of a patient's anatomy together in conjunction with other structural pieces, such as plates or flanges. When using these screws or other fasteners in these procedures, it is imperative that the fasteners be properly positioned in order to achieve the proper result from the procedure. Thus, often the physician will use wire guides to indicate where a particular fastener will be positioned prior to actually securing the fastener to the patient to ensure that the fastener is in the proper location.

To utilize these guide wires, a number of different types of devices are employed to properly hold the wires while the wires are positioned within the patient, as well as to engage or remove the wires from the patient. However, prior art devices used for this purpose utilize complex locking mechanisms to securely hold the wire, such as three jaw collets, or rotatable chucks, which can often make the tools difficult to use, especially during delicate surgical procedures.

Therefore, it is desirable to develop a tool that can be used to hold, engage and remove the wire that includes a wire engagement mechanism that enables the wire to be either grasped and held or released by the tool in a simple and easy to employ manner.

SUMMARY OF THE INVENTION

According to a one aspect of the present invention, a tool for releasably engaging a surgical guide wire is provided that includes a wire engagement mechanism having a single release member that is biased to engage a guide wire passing through the tool. To release the wire when desired, the engagement mechanism is simply pressed inwardly with regard to the remainder of the tool, and thereby disengaged from the wire. Also, due to the biasing force exerted on the engagement mechanism, the mechanism can be disengaged from the wire using only one hand, thereby allowing the physician to hold and steady the tool with the remaining hand. Also, the tool can be simultaneously held and have the engagement mechanism disengaged from the wire with only one hand, allowing the physician to use the remaining hand to perform some other function.

According to another aspect of the present invention, the engagement mechanism on the guide wire tool can be adjusted to provide different levels of biasing force to the engagement mechanism. As a result, the tool can be configured for use in a particular procedure, and for use with particular wires or other structures to be used in the procedure. This is particularly useful when the tool is also employed to drive and/or remove the guide wire, such that the engagement mechanism can securely hold the wire as the tool is used to move the wire with respect to the patient.

Numerous other aspects, features, and advantages of the present invention will be made apparent from the following detailed description together with the drawings figures.

BRIEF DESCRIPTION OF THE DRAWINGS

The drawings illustrate the best mode currently contemplated of practicing the present invention.

In the drawings.

DETAILED DESCRIPTION OF THE INVENTION

Figure 1:
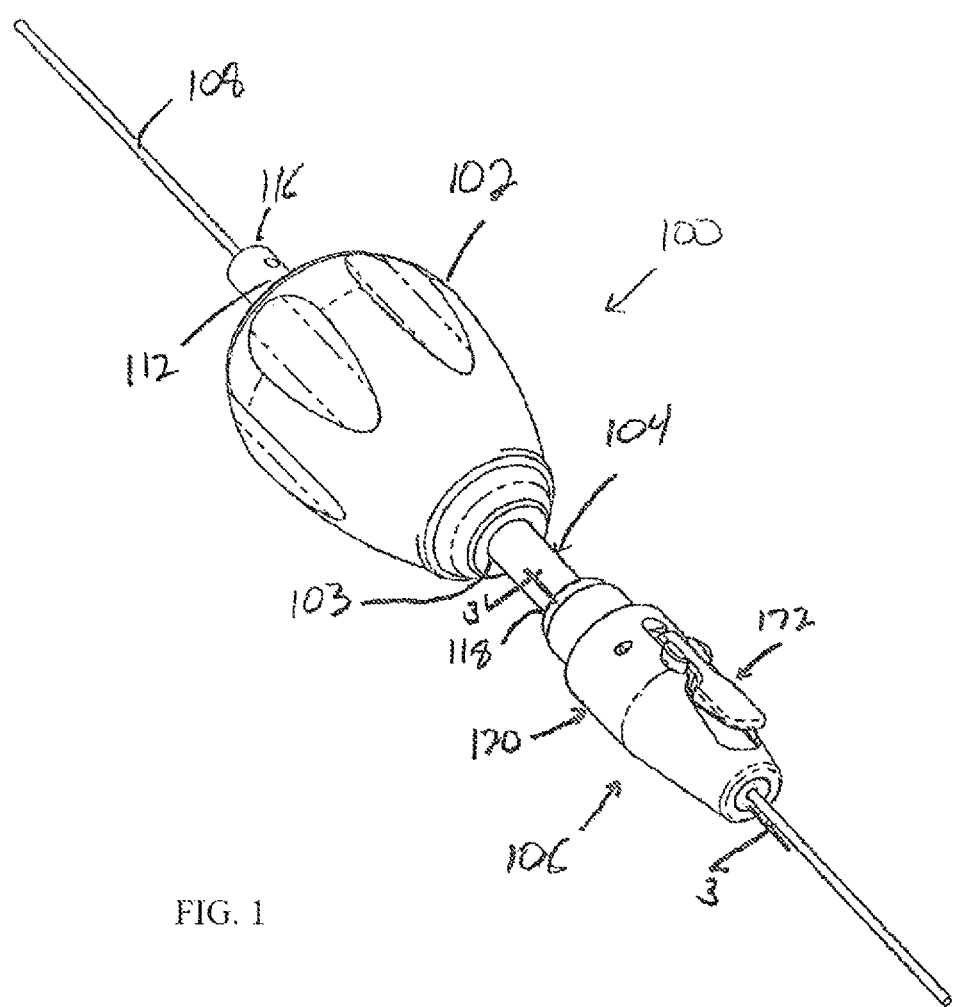
FIG. 1 is an isometric view of a guide wire positioning tool including the wire engagement mechanism constructed according to the present invention.
Figure 2:
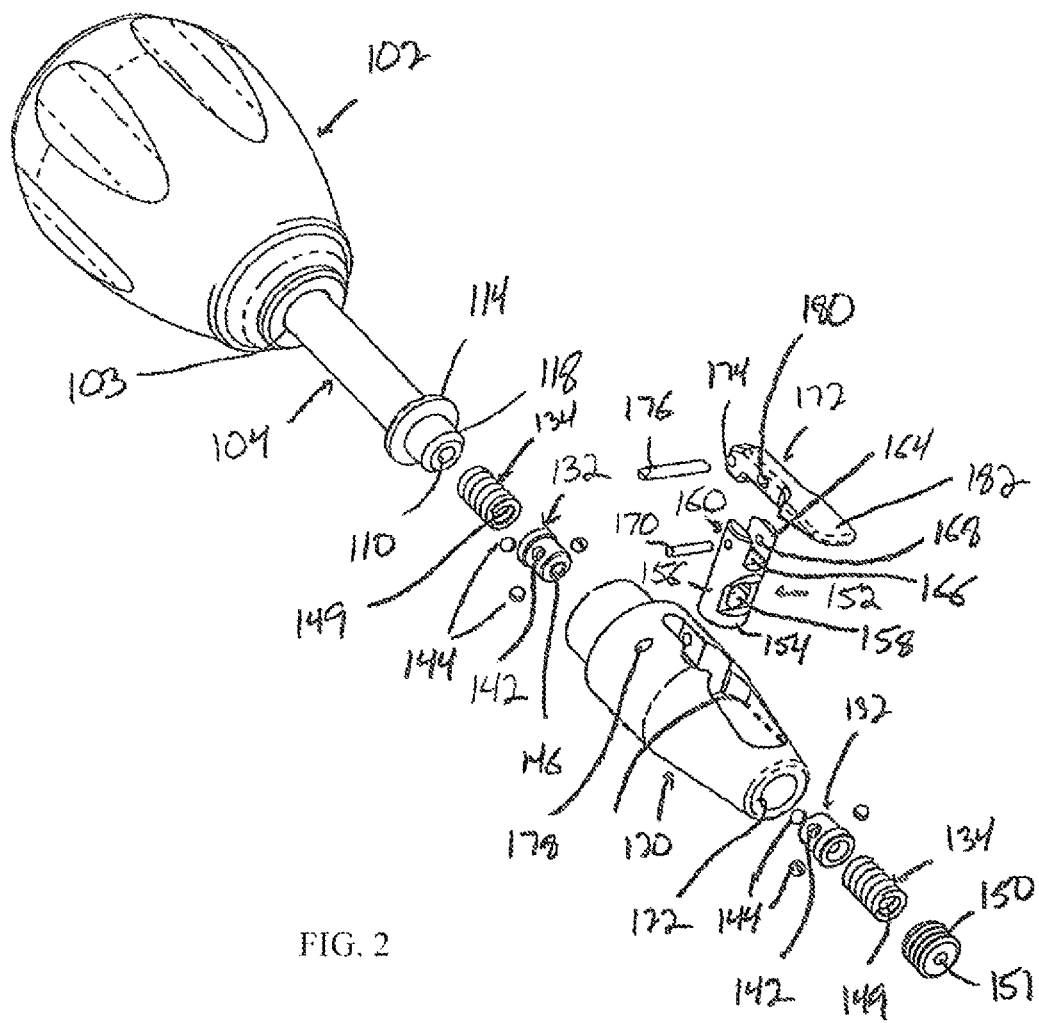
FIG. 2 is an exploded view of the tool and engagement mechanism of FIG. 1.

With reference now to the drawing figures in which like reference numerals designate like parts throughout the disclosure, a guide wire positioning tool constructed according to the present invention is indicated generally at 100 in FIGS. 1 and 2. The tool 100 includes a handle 102 mounted to one end of a shaft 104 that is secured opposite the handle 102 to a wire engagement mechanism 106. The handle 102 has a through-bore 103 that is disposed around the shaft 104 to mount the handle 102 to the shaft 104. The handle 102 can have any desired shape in order to make the handle 102 easy to hold and manipulate, and is preferably mounted to the shaft 104 such that the handle 102 can freely slide and/or rotate along the shaft 104 to provide a "tapping" function when a guide wire 108 engaged by the tool 100 is to be driven into or removed from a patient. However, it is also contemplated that the handle 102 can be fixed to the shaft 104, when desired, or removably attached to the shaft 104 to enable handles 102 of varying configurations to be secured to the shaft 104 to enable the tool 100 to be utilized in varying situations and environments.

Looking now at FIGS. 1 and 2, the drive shaft 104 is essentially formed as a hollow tube with a central passage 110 through which the wire 108 can pass. Also, depending upon the manner in which the handle 102 is attached to the shaft 104, the shaft 104 can have a pair of stops 112, 114 disposed at opposite ends 116, 118 of the shaft 104, such that the handle 102 is maintained on the shaft 104 between the stops 112, 114 when slidably mounted to the shaft 104. Additionally, the stops 112, 114 are preferably positioned inwardly from the ends 116, 118 of the shaft 104, so that one of the ends 116, 118 can be utilized to secure the shaft 104 to the wire engagement mechanism 106.

Figure 3:
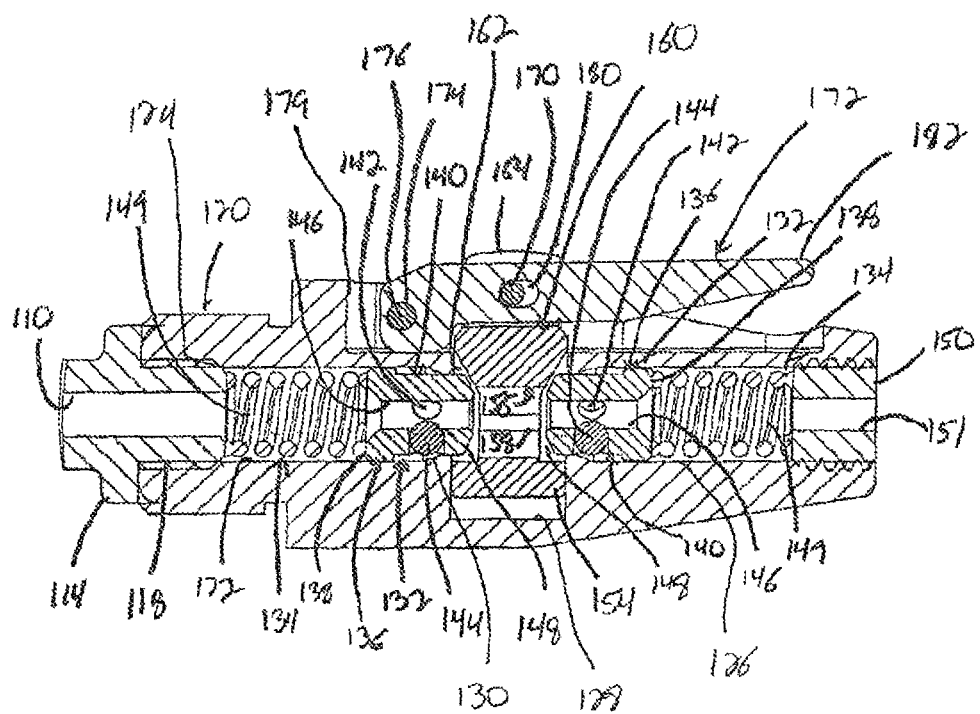
FIG. 3 is a cross-sectional view along line 3-3 of FIG. 1.

Referring now to FIGS. 1-3, the wire engagement mechanism 106 includes a housing 120 that defines a channel 122 therethrough. The channel 122 includes a pair of opposed end sections 124, 126 located at opposite ends of the housing 120, and a central section 128 disposed between the end sections 124, 126.

Each end section 124, 126 is generally circular in cross section along the longitudinal axis of the housing 120, with an inwardly tapering portion 130 located immediately adjacent the central section 128. The end sections 124, 126 each house a ferrule or collet 132 and a spring member 134. The collet 132 is formed with a wide end 136 defining a flange 138, and a narrow end 140. The narrow end 140 includes a number of apertures 142 formed therein in which are disposed bearings 144, which are preferably circular ball bearings. The apertures 142 intersect a bore 146 that extends completely through the collet 132 and is positioned in alignment with the channel 122 of the housing 120 when the collets 132 are disposed in the end sections 124, 126. The narrow end 140 of each collet 132 has a diameter that enables the narrow end 140 to pass through the tapering portion 130 of each end section 124, 126 and partially into the central section 128. Also, opposite the wide end 136, the narrow end 140 has a sloped surface 148 surrounding the bore 146.

The spring members 134 are preferably coil springs that each defines a passage 149 therethrough that is aligned with the bore 146 in the collet 132 and the channel 122 in the housing 120. Further, the springs 134 are each disposed in engagement with the flange 138 on the wide end 136 of the adjacent collet 132, and are in contact opposite the collet 132 with either the end 118 of the shaft 104 engaged with the housing 120, or with an end cap 150 engaged with the housing 120 opposite the shaft 104 and including a central passage 151 therein disposed in alignment with bore 103, channel 122, bores 146, and passages 149. The end 118 of the shaft 104 and the end cap 150 can be adjusted within the channel 122 to alter the amount of compressive force exerted on the spring members 134, thereby altering the amount of force required to move the collets 132 against the bias of the springs 134. This is preferably accomplished by making the end cap 150, movably and more preferably threadedly engageable within the channel 122 in the housing 120, such that any additional turning of the end cap 150 into or out of the channel 122 will correspondingly affect the compressive force from the spring 134 acting against movement of the collet 132. The end 118 of the shaft 104 can also be adjusted within the channel 122 in any suitable manner to affect the compressive force of the adjacent spring member 134 in a similar manner, if desired.

Within the central section of the channel 122 is disposed a plunger 152. The plunger 152 has a lower portion 154 that corresponds generally in shape to the cross section of the central section 128, such that the lower portion 154 can guide the movement of the plunger 152 within the central section 128. The plunger 152 also includes a central portion 156 that is narrower in diameter than the lower portion 154 and that defines an aperture 158 therein that can be positioned in alignment with the through-bore 103, the bores 146 in the collets 132, the passages 149 in the spring members 134, the passage 151 in end cap 150, and the channel 122 in the housing 120.

Opposite the lower portion 154, the central portion 156 is connected to an upper portion 160 that has a diameter similar to that of the lower portion 154 and an inwardly tapering wall 162 extending to the central portion 156. The upper portion 160 extends outwardly from the central section 128 of the channel 122 and includes a pair of opposed flanges 164 defining a notch 166 therebetween. Each flange 164 includes an opening 168 therein that receives one end of a pin 170 positioned across the notch 166 to movably secure a release member or trigger 172 to the plunger 152.

The trigger 172 includes a first end having a bore 174 formed therethrough and in which a pivot pin 176 is disposed. The pivot pin 176 is affixed at opposite ends within a passage 178 formed in the housing 120 in a direction generally perpendicular to the channel 122. The passage 178 crosses a recess 179 formed in the housing 120 above, and in alignment with the channel 122, and in which the trigger 172 is partially disposed to provide the trigger 172 and tool 100 with a reduced cross-sectional profile to enhance the ease of operation of the tool 100. Opposite the pivot pin 176, the trigger 172 extends outwardly from the recess 179, including a pin opening 180 through which pin 170 extends to connect the trigger 172 to the plunger 152, and an engagement portion 182 located opposite the pivot pin 176.

In operation, initially the engagement portion 182 of the trigger 172 is pressed towards the housing 120, thereby urging the plunger 152 into the central section 128 of the channel 122. This, in turn, causes the inwardly tapering wall 162 on the upper portion 160 to engage the sloped surfaces 148 on each collet 132. When the force exerted on the trigger 172 and plunger 152 is sufficient to overcome the force exerted by the spring member 134, the upper portion 160 of the plunger 152 urges the collets 132 out of the central section 128 against the bias of the spring members 134. As the collets 132 are moved in this direction, the ball bearings 144 can move out of the apertures 142 as the end sections 124, 126 of the channel 122 widen from the inwardly tapering portion 130. When the collet 132 has been moved a sufficient distance within the end sections 124, 126 to displace the bearings 144 sufficiently out of the bore 146, the wire 108 can be inserted completely through the tool 100, namely through the bore 103 in the shaft 104, the bores 146 in the collets 132, the passages 149 in the spring members 134, the passage 151 in the end cap 150, and the aperture 158 in the plunger 152. When the trigger 172 is released, the spring members 134 urge the collets 132 back into the central section 128, causing the bearings 144 to move along the tapering portions 130 of the end sections 124, 126 and to re-enter the apertures 142, consequently engaging the wire 108 therein. This engagement between the bearings 144 and the wire 108 securely retains the wire 108 at that position with regard to the tool 100, such that the wire 108 can be driven into or removed from the patient in any suitable manner, such as by using a handle 102 slidably mounted to the shaft 104.

When it is desired to remove the wire 108 from the tool 100, or to adjust the position of the wire 108 with regard to the tool 100, or vice versa, the trigger 172 is again depressed towards the housing 120 to effect the displacement of the collets 132 and bearings 144 in the manner described previously, such that the bearings 144 no longer contact the wire 108, which can then move freely through the entire tool 100.

In addition, when the wire 108 is securely engaged by the bearings 144, when the handle 102 is slidably mounted to the shaft 104, the tool 100 can be utilized to adjust or drive the wire 108 into the desired position. This is accomplished by sliding the handle 102 away from the housing 120, and subsequently driving the handle 102 towards the housing 120, where the handle 102 forcefully strikes the stop 114. The force of the handle 102 striking the stop 114 is transmitted through the housing 120, to which the stop 114 is connected, and onto the wire 108 to urge the wire 108 into the substrate within which it is positioned. This "tapping" motion can be repeated by the individual to move the wire 108 into the desired position, at which point the tool 100 can be disengaged from the wire 108 in the manner described previously and removed from the wire 108.

With regard to each of the components of the tool 100, because the tool 100 is utilized in surgical procedures, the components are each preferably formed from fluid-impervious and sterilizeable materials, such as stainless steel or other suitable materials well known to a person of ordinary skill in the art. Further, the tool 100 can be constructed with only a single collet 132 and spring 134 used to engage the wire 108. Also, in addition to wires, the tool 100 can be utilized to engage and position other elongate members within other substrates.

Various other embodiments of the present invention are contemplated as being within the scope of the filed claims particularly pointing out and distinctly claiming the subject matter regarded as the invention.

The invention claimed is:

1. A releasable engagement mechanism for an elongate member placement and removal tool, the mechanism comprising:
   a) a housing adapted to receive a portion of an elongate member therethrough;
   b) at least one moveable engagement member disposed within the housing and adapted to securely engage the portion of the elongate member positioned within the housing; and
   c) a release member engaged with the housing, wherein the release member is selectively engageable with the at least one moveable engagement member in a direction perpendicular to a direction of movement of the at least one moveable engagement member within the housing to disengage the at least one moveable engagement member from the elongate member to enable the elongate member to move freely with regard to the housing, wherein the at least one moveable engagement member is biased into engagement with the elongate member by a spring member disposed in alignment with the at least one engagement member and wherein the spring member is adapted to receive the elongate member therethrough.

2. The mechanism of claim 1 wherein the release member comprises:
   a) a plunger disposed within the housing and including an aperture through which the elongate member can extend; and
   b) an operating member movably connected to the plunger and to the housing and operable to move the plunger into and out of engagement with the at least one engagement member.

3. The mechanism of claim 2 wherein the operating member is at least partially disposed within a recess in the housing.

4. A releasable engagement mechanism for an elongate member placement and removal tool, the mechanism comprising:
   a) a housing adapted to receive a portion of an elongate member therethrough;
   b) a moveable engagement member disposed within the housing and adapted to securely engage the portion of the elongate member positioned within the housing; and
   c) a release member engaged with the housing, wherein the release member is selectively engageable with the moveable engagement member to disengage the moveable engagement member from the elongate member to enable the elongate member to move freely with regard to the housing, wherein the moveable engagement member is biased into engagement with the elongate member by a spring member disposed in alignment with the engagement member and wherein the spring member is adapted to receive the elongate member therethrough, and further wherein the at least one engagement member comprises:
   i) a cylindrical member including at least one aperture in a side wall of the cylindrical member; and
   ii) a bearing movably disposed within the at least one aperture.

5. A guide wire placement and removal tool comprising:
   a) a shaft;
   b) a handle mounted to the shaft; and
   c) a wire engagement mechanism secured to the shaft opposite the handle, the mechanism including a housing engaged with the shaft and adapted to receive a portion of a guide wire therethrough, a moveable engagement member disposed within the housing and adapted to securely engage the portion of the guide wire positioned within the housing, and a release member engaged with the housing, wherein the release member is selectively engageable with the moveable engagement member to disengage the moveable engagement member from the guide wire to enable the guide wire to move freely with regard to the housing, and wherein the handle is moveably mounted to the shaft.

6. The tool of claim 5 wherein the shaft includes a passage therethrough disposed in alignment with the housing.

7. The tool of claim 5 wherein the at least one moveable engagement member is biased into engagement with the elongate member by a spring member.

8. The mechanism of claim 5 wherein the release member comprises:
   a) a plunger disposed within the housing and including an aperture through which the elongate member can extend; and
   b) an operating member movably connected to the plunger and to the housing and operable to move the plunger into and out of engagement with the at least one engagement member.

9. The tool of claim 5 wherein the wire engagement mechanism includes a first movable engagement member disposed at one end of the housing and a second movable engagement member disposed at the other end of the housing.

* * * * *